United States Patent [19]

Saperstein

[11] 4,182,926
[45] Jan. 8, 1980

[54] CATALYTIC PROCESS FOR OBTAINING METHANE FROM METHANOL

[75] Inventor: David D. Saperstein, Mountainside, N.J.

[73] Assignee: Merck & Co., Inc., Rahway, N.J.

[21] Appl. No.: 944,502

[22] Filed: Sep. 21, 1978

[51] Int. Cl.² .............................................. C07C 1/20
[52] U.S. Cl. ................................. 585/733; 48/197 R
[58] Field of Search ................... 260/676 R, 449.6 M; 48/197 R

[56] References Cited

U.S. PATENT DOCUMENTS

| | | | |
|---|---|---|---|
| 4,021,370 | 5/1977 | Harris et al. | 48/197 R |
| 4,032,556 | 6/1977 | Banks | 260/449.6 M |
| 4,055,511 | 10/1977 | Elion et al. | 252/435 |
| 4,055,514 | 10/1977 | Elion et al. | 252/470 |
| 4,134,907 | 1/1979 | Stephens | 260/676 R |
| 4,139,551 | 2/1979 | Ozyagciler | 260/449.6 M |

OTHER PUBLICATIONS

C.A. 83, 88643, (1975).
C.A. 85, 23483, (1976).
C.A. 85, 179971, (1976).
C.A. 86, 4919, (1977).

Primary Examiner—C. Davis
Attorney, Agent, or Firm—Edmunde D. Riedl; Mario A. Monaco

[57] ABSTRACT

Methanol is vaporized at a temperature of from about 200° C.–455° C. and passed over a cobalt molybdate catalyst or a doped cobalt molybdate catalyst at a flow rate of from 60–200 cc./minute. The effluent gas comprises essentially methane and hydrogen in addition to some water vapors and $CO_2$.

6 Claims, No Drawings

CATALYTIC PROCESS FOR OBTAINING METHANE FROM METHANOL

DISCLOSURE OF THE INVENTION

This invention relates to a catalytic process for obtaining methane from methanol. More particularly, it relates to a process wherein a methanol or a methanol water mixture is passed over a heated catalyst which comprises cobalt molybdate or a metal doped cobalt molybdate.

Methane is an important building block in organic reactions used in industry as well as an important fuel source. Previously, it was abundantly obtained from natural gas wells at moderate expense. As natural gas supplies decrease and become increasingly scarce and methane recovery costs increase, it appears that other sources of methane are now required. One such process is synthesis from methanol which can be derived from bio-mass sources. However, present processes for conversion of methanol to methane do not achieve a reasonable conversion rate of methanol. This inefficiency shows how conversion necessitates using excessive amounts of methanol to make the desired amount of methane. I have now discovered that methane can be obtained cheaply from a methanol source in accordance with this invention which employs passing methanol over a heated cobalt molybdate catalyst.

The most efficient chemical product of methane from methanol producing the methane in 75% theoretical yield can be written as follows:

$$4CH_3OH \rightarrow 3CH_4 + CO_2 + 2H_2O$$

Other stoichiometric equations showing the conversion of methanol to methane exist, however, yet this is the most efficient. As a part of this invention, I show a near theoretical yield, i.e., 73% based on carbon (Example 2), for my process.

According to my invention, a reactant gas stream comprising methanol or methanol and water is passed over a cobalt molybdate catalyst at a temperature of at least 200° C. and more suitably 300° C. to 455° C.

As used herein the term "cobalt molybdate catalyst" includes those forms of that catalyst that are commercially available as well as the known cobalt molybdate catalysts doped with such material as chromium, vanadium, iron, phosphorus, boron and potassium. The technique of doping catalysts is well known and need not be reiterated except to acknowledge that the preferred catalyst is the chromium cobalt molybdate catalyst described in U.S. Pat. No. 4,055,511.

In carrying out the process of my invention a gas stream comprising the methanol, more suitably methanol and water preferably from 10%–50% by weight water is preheated to a temperature preferably in excess of 300° C. but not necessarily as a longer contact between gas and catalyst can compensate for the lower temperature. Lower temperatures are satisfactory provided a longer contact time is permitted. Thus, temperatures of from 200° C. upwards will provide good conversion provided the contact time is extended to the longer end of the range, e.g., 1.0 second or longer.

Temperatures as high as 455° C. are also satisfactory and have the advantage of requiring the shortest contact time, e.g. 0.05 seconds. It should be understood that each temperature in the permissible range has an optimum contact time for maximum yield. Such parameters are easily obtainable by those skilled in the art. After preheating, the gas stream is diluted with inert gas such as nitrogen, carbon dioxide, helium, argon and the like and directed over the heated catalyst bed. The residency time need be only 0.05 to 0.2 second, a longer time not, however, being deleterious. Generally, a contact time of 1 to 0.05 second is most suitable. While passing the methanol containing gas stream over a heated bed is preferred because of the simplicity of the process any other contact procedures such as countercurrent flow in a moving or fluidized bed is also satisfactory.

In most cases, there is an incomplete conversion of methanol to methane. Thus, as is conventional, the exit gas stream is cooled to condense unreacted methanol which is then recycled.

The following specific examples are further illustrative of my process.

EXAMPLE 1

200–1,000 Microliters of a 15%–100% (v/v) methanol-water solution is vaporized in a 360° C.–420° C. heater at a rate of 15–100 microliters/minute. The vaporized stream is diluted with helium or nitrogen flowing at a rate of 60–200 cc./minute. This stream contacts the 360° C.–420° C. catalyst for a residence time of 0.05–0.2 seconds. The total effluent from the microreactor is passed through heated lines to the online analyzer—a Nicolet 7199 FT-IR equipped with a heatable, gold coated, light pipe for measuring gases and additionally was collected for off-line gas chromatographic analysis.

EXAMPLE 2

160 Mg. of methanol in 400 microliters of an aqueous solution was passed through a 420° C. bed of unsupported chromium cobalt molybdate, see U.S. Pat. No. 4,055,511 for preparation details, at a rate of 40 mg./minute having a catalyst residence time of 0.1 second. The product gases which were analyzed without further treatment contained 28% methanol as well as 31% $CH_4$, 30% $H_2$, 11% $CO_2$ and a trace of CO.

EXAMPLE 3

214 Mg. of methanol in 400 microliters of an aqueous solution was passed through a 420° C. bed of unsupported chromium cobalt molybdate (prepared as in Example 2) at a rate of 54 mg./minute having a catalyst residence time of 0.05 second. The product gases which were analyzed without further treatment contained 60% methanol as well as 1% $CH_4$, 14% $H_2$, 5% $CO_2$ and 2% CO.

EXAMPLE 4

48 Mg. of methanol in 175 microliters of an aqueous solution was passed through a 420° C. bed of a chromium doped cobalt molybdate at a rate of 4 mg./minute having a residence time of 0.2 second. The effluent gases which were analyzed on line showed the carbonaceous products to be in the molar ratio: $CH_4/CO_2/CO$:2.35/1.0/0.1.

EXAMPLE 5

In four separate experiments a 40% (v/v) solution of methanol in water was passed through a hot catalyst bed at a rate of 5 mg./minute having a catalyst residence time of 0.2 second. The conversion of methanol to methane, exclusive of other products, under the following conditions was:

|  | Methanol Converted | Methane Formed |
|---|---|---|
| (1) Cobalt molybdate, 360° C. | 11% | 5% |
| (2) Cobalt molybdate, 420° C. | 39% | 20% |
| (3) Chromium cobalt molybdate 360° C. | 26% | 11% |
| (4) Chromium cobalt molybdate 420° C. | 66% | 47% |

% based on carbon

Once obtained the methane can be separated from unreacted methanol and other gases that may be present by any of many well known techniques such as scrubbing, adsorbtion on molecular sieves, or other chemical absorbants.

What is claimed is:

1. A process for producing methane comprising passing a gas stream comprising methanol at a temperature of at least 200° C. into contact with a cobalt molybdate catalyst heated to at least 200° C. for a contact time of at least 0.01 second; separating the methane from any residue of unreacted methanol.

2. A process according to claim 1 wherein the catalyst bed is heated to a temperature of from 350° C. to 455° C.

3. A process according to claim 1 wherein a chromium cobalt molybdate catalyst is employed.

4. A process according to claim 1 wherein the temperature of the gas stream is from 200° to 455° C.

5. A process according to claim 1 wherein a contact time of the gas stream over the catalyst is from 0.2 to 0.05 second.

6. A process according to claim 1 wherein there is included in said gas stream from 10% to 50% by weight of water.

* * * * *